United States Patent [19]

Ozawa et al.

[11] 4,042,638

[45] Aug. 16, 1977

[54] PROCESS FOR PREPARING OLIGOMERS OF HEXAFLUOROPROPENE

[75] Inventors: Masahiro Ozawa, Kamifukuoka; Tadaaki Komatsu, Saitama; Kimiaki Matsuoka, Kawagoe, all of Japan

[73] Assignee: Central Glass Co., Ltd., Ube, Japan

[21] Appl. No.: 676,494

[22] Filed: Apr. 13, 1976

[30] Foreign Application Priority Data

Apr. 17, 1975  Japan .................................. 50-45818

[51] Int. Cl.$^2$ ........................ C07C 21/18; C08F 14/28
[52] U.S. Cl. ............................................ 260/653.1 R
[58] Field of Search ................................ 260/653.1 R

[56] References Cited

U.S. PATENT DOCUMENTS

| | | | |
|---|---|---|---|
| 3,403,191 | 9/1968 | Graham | 260/653.1 R |
| 3,917,724 | 11/1975 | Martini | 260/653.1 R |

*Primary Examiner*—Delbert E. Gantz
*Assistant Examiner*—J. Thierstein
*Attorney, Agent, or Firm*—Fleit & Jacobson

[57] ABSTRACT

Oligomers of hexafluoropropene are prepared by oligomerization of hexafluoropropene in an organic solvent in the presence of a halide compound and a crown ether. The selectivity to the dimer or trimer may vary depending on the kind of solvent. For example, the oligomerization of hexafluoropropene in acetonitrile or methylene chloride in the vicinity of room temperature gives the dimer thereof at high selectivity. Use of N,N-dimethylformamide favors the formation of the trimer at high selectivity.

19 Claims, No Drawings

PROCESS FOR PREPARING OLIGOMERS OF HEXAFLUOROPROPENE

This invention relates to a process for preparing oligomers of hexafluoropropene, and more particularly to a process for selectively preparing a dimer or trimer of hexafluoropropene.

Oligomers of hexafluoropropene are known to be useful as media or solvents under high temperature conditions or as starting materials for water or oil repellents and various kinds of industrial surfactants. In recent years, many processes for the production of oligomers of hexafluoropropene have been developed and proposed including: a provess of preparing an oligomer by treating hexafluoropropene in solvent at a temperature of 0° to 200° C under pressure in the presence of halides, hydroxides or quaternary ammonium salts of metals of Group I of the Periodic Table (United States Pat. No. 2,918,501); a process of oligomerizing hexafluoropropene in non-protolytic polar solvent in the presence of trimethylamine (Chem. Commun. 1444 (1970)); and a process which comprises oligomerizing hexafluoropropene in the presence of acetonitrile solvent and a catalyst such as potassium fluoride under pressure in the vicinity of 100° C, thereby obtaining a dimer thereof at a selectivity of 93 to 95% (Japanese Patent Publication No. 134614/1974). However, these processes have a disadvantage that high temperature and high pressure are essentially required to ensure high rate of reaction for industrial production of the oligomers. In addition, the oligomers obtained by these processes are generally in the form of either a mixture of the dimer and trimer or a dimer alone.

Further, the selective production of a dimer or trimer of hexafluoropropene in the vicinity of room temperature has been proposed using a fluorine-containing tertiary amine catalyst and acetonitrile solvent (Japanese Patent Publication No. 110607/d1974). However, this process is disadvantageous in that a specific compound of a fluorine-containing tertiary amine is required in a large amount and that produced oligomers must be separated by distillation due to its solubility in the amine.

It is therefore an object of the present invention to provide a process for preparing oligomers of hexafluoropropene which overcomes the disadvantages of the prior processes.

It is another object of the present invention to provide a process for preparing oligomers of hexafluoropropene which is high in yield and excellent in selectivity to the dimer or trimer thereof.

It is a further object of the present invention to provide a process for the oligomerization of hexafluoropropene under relatively mild reaction conditions and at an industrially satisfactory rate of reaction.

The above and other objects and advantages of the present invention will be apparent from the description thereof which follows.

The above objects of the present invention has been achieved by subjecting hexafluoropropene to oligomerization reaction in an organic solvent in the presence of a halide compound and a crown ether. For selective production of hexafluoropropene dimer, the oligomerization reaction should be effected in an acetonitrile or methylene chloride solvent in the vicinity of room temperature, whereby the dimer is obtainable at a selectivity higher than 99%.

Usable halide compounds include metal halides, particularly alkali metal halides, ammonium halides, quaternary ammonium halides and the like. Examples of suitable halide compounds are potassium fluoride, cesium fluoride, potassium chloride and the like. These halide compounds and crown ethers are used only in catalytic amounts. The halide compound and crown ether readily form a complex salt thereof which serves as the catalyst for hexafluoropropene. It is assumed that upon formation of a complex salt with a halide compound, the crown ether exerts a strong trapping action (or coordination action) on cations, e.g., potassium ions or ammonium ions, of the halide compound, taking the cations in its holes. This assists in accelerating the dissociation of corresponding anions of the halide to impart to the anions a considerably increased nucleophilic ability. Accordingly, the choice of a crown ether should preferably depend on the kind of the halide compound so that the chosen crown ether has a diameter of holes sufficient for receiving cations of the halide compound.

The term "crown ether" used herein is understood to imply all of macrocyclic ethers (oxygen of which may be at least partially substituted with nitrogen, sulfur or phosphorus ) which have functions of aggressively coordinating cations within its holes and of activating corresponding anions in a catalytic sense. The macrocyclic ethers are, for example, a group of cyclic polyethers as defined by C. J. Pedersen in the Journal off the American Chemical Society (89, pages 7017–7036) which are incorporated herein by reference. Examples of the crown ethers suitable for the practice of the invention include, according to a simplified nomenclature by C. J. Pedersen et al, decalyl-15-crown-5, dibenzo-14-crown-4, dibenzo 20-crown-4, dibenzo -18-crown-5, asym-dibenzo-19-crown-5, 18-crown-6,dibenzo-18-crown- 6, dicyclohexyl-18-crown-6, asym-dicyclohexyl-48-crown-16, asym-dibenzo-22-crown-6, dibenzo-26-crown-6, benzo-15-crown-5, dibenzo-24-crown-8, etc., compounds obtaining by substituting a part or all of oxygen atoms of the above-indicated cyclic polyethers with sulfur. Of these, 18-crown-6 compounds including 18- crown-6, dibenzo-~-crown-6, and dicylohexyl-18-crown-6 are preferred since they are easy to prepare. Further there may be also used another type of crown ether compounds or cryptate compounds expressed by the following general formula

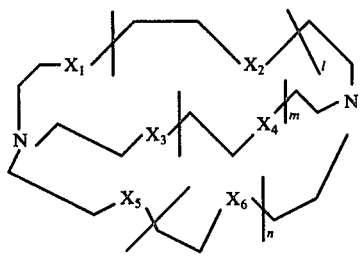

wherein 1, $m$ and $n$ are independently an integer of from 1 to 5, and $X_1$, $X_2$, $X_3$, $X_4$, $X_5$ $X_6$ are indenpendently O, S or R-N in which R represents an alkyl group containing from 1 to 5 carbon atoms.

Examples of the cryptate compounds include 4, 7, 13, 16, 21, 24-hexaoxy-1, 10-diazabicyclo hexacosane

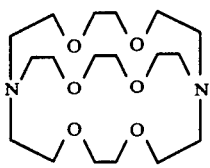

4, 7, 13, 16, 21-pentaoxa-1,10-diazabicyclo tricosane having a formula

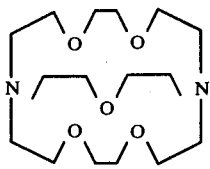

4, 7, 13, 18-tetraoxa-1,10-di-azabicyclo [8, 5, 5] eicosane having a formula

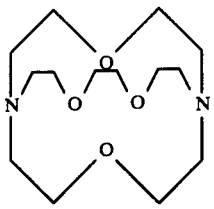

and the like. The crown ethers and the compounds of the above general formula can be prepared by a known method as described in the above-mentioned literature.

It is the practice of the present invention hexafluoropropene is fed for oligomerization into an organic solvent containing the catalyst with agitation under a normal pressure of a slightly elevated pressure at a reaction temperature of −20° to 200° C, preferably 0° to 100° C. If desired, the reaction system may be cooled to remove the heat of reaction. The halide compounds used as the catalyst in combination with the crown ether are preferred to be alkali metal halides, particularly potassium fluoride, cesium fluoride and potassium choride. The concentration of the catalyst is not critical with regard to its upper limit. The alkali metal halide is desired to be in concentration greater than 0.001 mol/l of solvent and the crown ether in a concentration by mol of above 1/50 time that of the employed alkali metal halide. The concentration below the above-defined ranges are disadvantageous economically and industrially in view of a material drop in the rate of reaction As described hereinbefore, through the reaction temperature is generally in the range of −20° to 200° C, preferably 0° to 100° C, it should be varied within the above range depending on the kind and concentration of catalyst, kind of solvent, composition of the desired oligomer product and so forth. Although the reaction in most cases takes several minutes to several hours to produce an appreciable amount of product, it should be realized that this time and the various other operating conditions for the reaction are interdependent. That is, the time of reaction, the temperature, pressure, concentrations of hexafluoropropene and catalyst, kind of catalyst and so forth are all related.

The solvents useful for the purpose of the invention include, for example, non-protolytic polar solvents such as N, N-dimethylformamide, dimethylsulfoxide, acetonitrile, etc., and non-polar solvents such as hydrocarbons including n-pentane, N-hexane, cyclohexane, etc., halogenated hydrocarbons including dichloroethylene, 1, 1, 1-trichloroethane, 1, 1, 2-trichloroethane, 1, 2, 2-trifluoroethane, etc., glymes including mono-, di-, tri- and tetra-ethylene glycol dimethyl ether, and ethers such as diethyl ether, tetrahydrofuran, dioxane, etc., though almost all of organic solvents which are inert under reaction conditions may be used in the oligomerization reaction of the invention.

In general, the rate of reaction and the composition of oligomer produced are greatly influenced by the kind of solvent. When, for example, acetonitrile or methylene chloride is used as solvent, the dimer is obtained in the vicinity of room temperature at a selectivity of 99% or more. In contrast, when N,N-dimethylformamide is used as solvent and the oligomerization reaction is conducted at about 90° C, the trimer is produced with a high yield in a selectivity of about 93.7%. Use of other organic solvents are suitable for the production of the oligomers in mixed form.

Though it is desirable to feed hexafluoropropene by an amount sufficient to be absorbed in the reaction system, it may be used in an excess amount, recovering the excessive hexafluoropropene which remains unreacted by any known methods for reuse.

The halide compound-crown ether complex, particularly an alkali metal halide-crown ether complex, may be produced without resorting to any special reaction techniques. That is, it will suffice to add to the reaction system predetermined amounts of an alkali metal halide and a crown ether with agitation. If necessary, an alkali metal halide and a crown ether may be mixed with each other in a separate reactor to prepare crystals of a complex thereof for addition to the reaction system. Preferred combinations of halide compounds and crown ethers are those which will be particularly exemplified in the following examples.

The present invention will be particularly illustrated by way of the following examples, which should not be construed as limitation thereof.

EXAMPLE 1

In a 100 cc pressure reactor of a glass tube type equipped with a gas feed port and a pressure gauge were placed 30 cc of methylene chloride, 0.005 mols of dry potassium fluoride and 0.001 mol of 18-crown-6 (i.e., 1, 4, 7, 10, 13, 16-hexaoxacyclooctadecane), followed by cooling to −76° C and complete degassing. The tube reactor was placed in an ice bath and the content was vigorously stirred for 20 min by means of a magnetic stirrer. Then, 15 g of hexafluoropropene was fed from the gas feed port into the reaction system while agitating under ice cooling conditions so that the reaction pressure was maintained in the range of 0 to 2.0 kg/cm² (gauge). The feed of hexafluoropropene was completed in about 15 minutes. The reaction was carried on for further 15 minutes and completed when the pressure reached −40 cmHg (gauge). The content in the reactor was transferred to a separating funnel to separate the lower oligomer layer from the upper layer thereby obtaining 13.08 g of an oligomer at a yield of 87.2% by weight. The oligomer was subjected to a gas chromatographic analysis, revealing that the oligomer was composed of 99.1% of dimer and 0.9% of trimer and that the dimer consisted of 95.8% of the trans isomer of the structure $(CF_3)_2CFCF=CFCF_3$ and 4.2% of a mixture of the cis isomer of the structure $(CF_3)_2CFCF=CFCF_3$ and a compound with the formula $(CF_3)_2C=CFCF_2CF_3$.

The above process was repeated using the reaction conditions indicated in Table 1. The test results are also shown in Table 1 below.

TABLE 1

| Ex. No. | solvent (30 cc) | alkali metal halide | amount by mol | amount by mol of 18-crown-6 | reaction temp. (° C) | reaction time (hr) | yield of oligomer (wt %) | selectivity (wt %) | |
|---|---|---|---|---|---|---|---|---|---|
| | | | | | | | | dimer | trimer |
| 2 | methylene chloride | KF | 0.005 | 0.002 | 40 | 1.0 | 86.4 | 81.9 | 18.1 |
| 3 | " | " | " | " | 20 | 0.5 | 77.7 | 91.0 | 9.0 |
| 4 | " | " | " | 0.00067 | 0 | 1.0 | 88.0 | 99.0 | 1.0 |
| 5 | " | CsF | " | 0.001 | 0 | 0.5 | 88.8 | 85.6 | 14.4 |

Note:
The reaction temperature means a bath temperature here and whenever it appears in the following examples.

The 18-crown-6 used in the above examples was prepared as follows. 112.5 g (0.75 mols) of the triethylene glycol and 600 cc of tetrahydrofuran (THF) were introduced into a 3l three-necked flask equipped with an agitator, a reflux condenser, and a dropping funnel, to which was added 109 g (1.65 mols) of 85% KOH dissolved in 70 cc of water with agitation. The agitation was continued for 15 minutes and then a mixture of 140.3 g (0.75 mols) of triethylene glycol dichloride and 100 cc of THF was added to the reaction system. After completion of the addition, the reaction system was agitated for further 18 hours while refluxing. After cooling, most of the THF was removed by distillation under reduced pressure to obtain about 200 cc of a concentrated reaction solution. To the concentrated solution was added 500 cc of methylene chloride ($CH_2Cl_2$), from which insoluble solid matter or slurry was removed by filtration. The resultant filtrate was dried with $Na_2SO_4$ and distilled under gradually decreasing reduced pressure. As a result, about 86 g of a distillate of 105° to 170° ClO4 mmHg was obtained. The distillate was placed in a 500 cc Erlenmeyer flask, to which was added 200 cc of acetonitrile for completely dissolving the resulting crystals by heating. When the hot solution was gradually cooled, acetonitrile-18-crown-6 complex was separated as crystals. The crystals were immediately filtered and subjected to a suction treatment under a reduced pressure of 5 mmHg for 16 hours for removing acetonitrile therefrom to obtain 50.5 g of white crystals (a yield of 25.5%).

The crystal product had a melting point of 37 to 38° C, and was analyzed and found to contain: C,54.4%, H,9.2%. The analyses calculated for $C_{12}H_{24}O_6$ C, 54.53%, H,9.15%. The curves of the infrared and NMR spectra of the product coincided with those of 18-crown-6, respectively.

EXAMPLES 6–8

Example 1 was repeated except that acetonitrile was used instead of methylene chloride and the reaction conditions as indicated in Table 2 were used. The test results are shown in Table 2 below.

TABLE 2

| Ex. No. | solvent (30 cc) | alkali metal halide | amount by mol | amount by mol of 18-crown-6 | reaction temp. (° C) | reaction time (hr) | yield of oligomer (wt %) | selectivity (wt %) | |
|---|---|---|---|---|---|---|---|---|---|
| | | | | | | | | dimer | trimer |
| 6 | acetonitrile | KF | 0.005 | 0.001 | 0 | 0.5 | 93.6 | 98.0 | 2.0 |
| 7 | " | " | " | 0.0013 | 30 | 1.0 | 82.8 | 91.0 | 9.0 |
| 8 | " | " | " | 0.0025 | 0 | 20 min. | 88.7 | 93.6 | 6.4 |

EXAMPLES 9–12

Example 1 was repeated using different kinds of solvents and different reaction conditions as indicated in Table 3. The test results are also shown in Table 3 below.

TABLE 3

| Ex. No. | solvent (30 cc) | alkali metal halide | amount by mol | amount by mol of 18-crown-6 | reaction temp. (° C) | reaction time (hr) | yield of oligomer (wt %) | selectivity (wt %) | |
|---|---|---|---|---|---|---|---|---|---|
| | | | | | | | | dimer | trimer |
| 9 | N,N'-dimethylformamide | KF | 0.005 | 0.001 | 90 | 1.0 | 88.6 | 6.3 | 93.7 |
| 10 | benzene | " | " | " | 95 | 1.5 | 78.8 | 31.2 | 68.8 |
| 11* | diglyme | " | " | " | 60 | 1.5 | 66.0 | 53.3 | 46.8 |
| 12* | tetrahydrofuran | " | " | " | 50 | 1.0 | 65.0 | 63.1 | 36.9 |

*The low yields of oligomers in Examples 11 and 12 are mainly due to the hexafluoropropene which remained unreacted, not due to formation of by-products.

COMPARATIVE EXAMPLES 1–5

The general procedures used in these Comparative Examples were similar to that described in Example 1 but the oligomerization reaction was effected, without use of 18-crown-6, using such reaction conditions, solvents and catalysts as indicated in Table 4. The experimental results are also shown in Table 4 below.

TABLE 4

| Comparative Example No. | solvent (30 cc) | alkali metal halide | amount by mol | reaction temp. (° C) | reaction time (hr) | yield of oligomer (wt %) | selectivity (wt %) | |
|---|---|---|---|---|---|---|---|---|
| | | | | | | | dimer | trimer |
| 1 | acetonitrile | KF | 0.005 | 20 | 3.0 | 0 | — | — |
| 2 | " | " | " | 85 | 2.5 | 38.3 | 72.9 | 27.1 |
| 3 | methylene chloride | " | " | 90 | 1.0 | 0 | — | — |
| 4 | " | CsF | " | 50 | 1.0 | 0 | — | — |
| 5 | " | KF | " | 95 | 3.0 | 46.6 | 51.9 | 48.1 |

EXAMPLE 13

Example 7 was repeated using dibenzo-18-crown-6 (0.001 mol) instead of 18-crown-6. As a result, hexafluoropropene oligomer was obtained at a yield of 90.3% and was composed of 90.0% of dimer and 10.0% of trimer. The dibenzo-18-crown-6 was prepared in accordance with the known method described in the Journal of the American Chemical Society (89, pages 7019-7036 (1967)).

EXAMPLE 14

20 cc of acetonitrile, 0.05 mols of potassium chloride and 0.001 mol of 18-crown-6 were introduced together with a stirrer into a 50 cc stainless steel autoclave equipped with a gas feed port. The autoclave was hermetically sealed, cooled to −78° C and degassed. Thereafter, 2.8 g of hexafluoropropene was fed into the autoclave through the gas feed port while cooling, after which the autoclave was again closed. The autoclave was placed in an oil bath maintained at a bath temperature of 130° to 150° C for 30 min while stirring by means of a magnetic stirrer. As a result, the reaction pressure was observed to be 4.5 kg/cm² (gauge) at a final stage of the reaction. The contents in the autoclave was transferred to a separating funnel to separate therefrom 1.0 g of an oligomer layer.

The yield was 35.7%. The oligomer was analyzed by a gas chromatography and found to be composed of 28.2% by weight of dimer and 71.8% by weight of trimer.

EXAMPLES 15-18

Example 6 was repeated using different kinds of crown ethers and action conditions as indicated in Table 5. The test results are also shown in Table 5 below.

TABLE 5

| Example No. | crown ether | amount by mol | reaction temp. (° C) | reaction time (hr) | yield of oligomer (wt %) | selectivity (wt %) | |
|---|---|---|---|---|---|---|---|
| | | | | | | dimer | trimer |
| 15 | benzo-15-crown-5- | 0.001 | 50 | 1.0 | 84.8 | 86.8 | 13.2 |
| 16 | dicyclohexyl-18-crown-6 | 0.001 | 0 | 0.5 | 92.0 | 95.1 | 4.9 |
| 17 | dibenzo-24-crown-8 | 0.001 | 0 | 0.5 | 78.5 | 98.9 | 1.1 |
| 18 | cryptate** | 0.0005 | 0 | 0.7 | 93.6 | 55.3 | 44.7 |

*Solvent: acetonitrile, 30 cc, alkali metal halide: KF, 0.005 moles.
**4,7,13,16,21,24-hexaoxy-1,10-diazabicyclo-(8,8,8)-hexacosane.

What is claimed is:

1. A process for preparing oligomers of hexafluoropropene comprising subjecting hexafluoropropene to an oligomerization reaction in the presence of an alkali metal halide and a crown ether at a reaction temperature of about from −20° C. to 200° C., said oligomerization reaction being carried out in an organic solvent which is inert under the oligomerization reaction conditions, said alkali metal halide being present in an amount greater than 0.001 mol per liter of said organic solvent and said crown ether being present in an amount greater than 1/50 time that of said alkali metal halide on a mol basis.

2. A process according to claim 1, wherein said reaction temperature is in the range of 0° C to 100° C.

3. A process according to claim 1, wherein said alkali metal halide and said crown ether are in the form of a complex.

4. A process according to claim 1, said alkali metal halide is potassium fluoride.

5. A process according to claim 1, wherein said alkali metal halide is cesium fluoride.

6. A process according to claim 1, wherein said alkali metal halide is potassium chloride.

7. A process according to claim 1, wherein said crown ether is a member selected from the group consisting of decalyl-15-crown-5, dibenzo-14-crown-4, dibenzo-20-crown-4, dibenzo-18-crown-5, asymdibenzo-19-crown-6, 18-crown-6, dibenzo-18-crown-6, dicyclohexyl-18-crown-6, asym-dicyclohexyl-48-crown-16, asym-dibenzo-22-crown-6, dibenzo-26-crown-6, benzo-15-crown-5, dibenzo-24-crown-8 and derivatives thereof in which a part of all of the oxygen contained therein is substituted with sulfur.

8. A process according to claim 7, wherein said crown ether is 18-crown-6.

9. A process according to claim 7, wherein said crown ether is dibenzo-18-crown-6.

10. A process according to claim 7, wherein said crown ether is dicyclohexyl-18-crown-6.

11. A process according to claim 1, wherein said crown ether is a compound expressed by the following formula

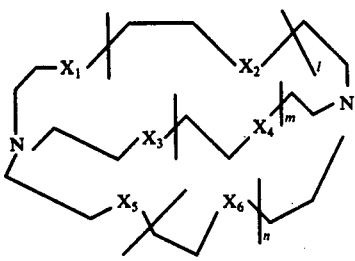

wherein $l$, $m$ and $n$ are independently an integer of from 1 to 5 and $X_1$, $X_2$, $X_3$, $X_4$, $X_5$ and $X_6$ are independently O, S or R-N in which R represents an alkyl group containing from 1 to 5 carbon atoms.

12. A process according to claim 1, wherein said solvent is a member selected from the group consisting of acetonitrile and methylene chloride.

13. A process according to claim 1, wherein said solvent is N,N-dimethylformamide.

14. A process for preparing a dimer of hexafluoropropene comprising subjecting hexafluorpropene to an oligomerization reaction in a solvent selected from the group consisting of acetonitrile and methylene chloride in the presence of an alkali metal halide elected from the group consisting of potassium fluoride, cesium fluoride, and potassium chloride and a crown ether in the vicinity of room temperature, said alkali metal halide being present in an amount greater than 0.001 mol per liter of said solvent and said crown ether being present in an amount greater than 1/50 time that of said alkali metal halide on a mol basis.

15. A process for preparing a trimer of hexafluoropropene comprising subjecting hexafluoropropene to an oligomerization reaction in N,N'-dimethylformamide in the presence of an alkali metal halide selected from the group consisting of potassium fluoride, cesium fluoride, and potassium chloride and a crown ether at a temperature of about 90° C., said alkali metal halide being present in an amount greater than 0.001 mol per liter of said N,N'-dimethylformamide and said crown ether being present in an amount greater than 1/50 time that of said alkali metal halide on a mol basis.

16. The process according to claim 1, wherein the organic solvent is selected from the group consisting of N,N-dimethylformamide, dimethylsulfoxide, methylene chloride, acetonitrile, hydrocarbons, halogenated hydrocarbons, glymes, and ethers.

17. The process according to claim 1, wherein the organic solvent is selected from the group consisting of acetonitrile, methylene chloride, N,N-dimethylformamide, dimethylsulfoxide, n-pentane, n-hexane, cyclohexane, benzene, 1, 1, 1-trichloroethane, 1, 1, 2-trichloroethane, 1, 2, 2-trifluoroethane, dichloroethylene, mono-, di-, tri-, and tetra-ethylene glycol dimethyl ether, diethyl ether, tetrahydrofuran, and dioxane.

18. The process according to claim 10, wherein the solvent is acetonitrile.

19. The process according to claim 16, wherein the solvent is methylene chloride.

* * * * *